(12) United States Patent
Cheng et al.

(10) Patent No.: US 8,426,039 B2
(45) Date of Patent: Apr. 23, 2013

(54) 9,10-BISPHENYLPHENANTHRENE DERIVATIVE AND ORGANIC LIGHT EMITTING DIODE USING THE SAME

(75) Inventors: Chien-Hong Cheng, Hsinchu (TW); Yu-Han Chen, Hsinchu (TW); Fang-Iy Wu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 198 days.

(21) Appl. No.: 13/030,676

(22) Filed: Feb. 18, 2011

(65) Prior Publication Data

US 2012/0104364 A1   May 3, 2012

(30) Foreign Application Priority Data

Oct. 29, 2010   (TW) ................. 99137256 A

(51) Int. Cl.
*H01L 51/50* (2006.01)
*C07C 13/54* (2006.01)

(52) U.S. Cl.
USPC ........... 428/690; 428/917; 313/504; 313/506; 585/26; 257/40

(58) Field of Classification Search ........... None
See application file for complete search history.

(56) References Cited

U.S. PATENT DOCUMENTS

2006/0228578 A1 * 10/2006 Ren et al. .............. 428/690
2010/0327230 A1 * 12/2010 Kawamura et al. ...... 252/301.16
2010/0331585 A1 * 12/2010 Kawamura et al. ........... 585/26

FOREIGN PATENT DOCUMENTS

| EP | 2189508 A2 | * | 5/2010 |
| JP | 2001-332384 | | 11/2001 |
| WO | WO 2009/008355 | * | 1/2009 |
| WO | WO 2009008341 A1 | * | 1/2009 |

* cited by examiner

*Primary Examiner* — Dawn Garrett
(74) *Attorney, Agent, or Firm* — Muncy, Geissler, Olds & Lowe, PLLC

(57) ABSTRACT

A 9,10-bisphenylphenanthrene derivative has a structure of formula (1):

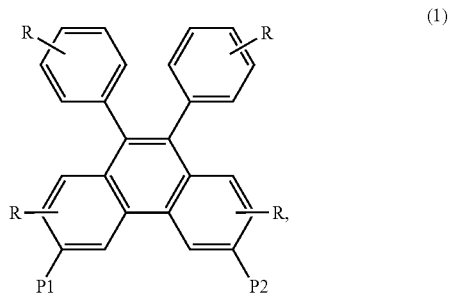

(1)

wherein P1 and P2 are substituted or non-substituted polycyclic aromatic hydrocarbons (PAH), and R is a member selected from the group consisting of H, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl. The 9,10-bisphenylphenanthrene derivative of the present invention may function as a host emitter to be used in an organic light emitting device with advantages such as higher efficiency, lower operating voltage, higher brightness and higher thermal stability.

11 Claims, 3 Drawing Sheets

9,10-BISPHENYLPHENANTHRENE DERIVATIVE AND ORGANIC LIGHT EMITTING DIODE USING THE SAME

BACKGROUND OF THE INVENTION

1. Field of the Invention

The present invention relates to a novel compound and organic light emitting diode using the same, particularly to 9,10-bisphenylphenanthrene derivatives and organic light emitting diode using the same.

2. Description of the Prior Art

OLED works on the principal that electrons and holes diffuse through an electron transport layer (ETL) and hole transport layer (HTL), respectively, to enter a light-emitting layer, and recombine in the emitting region to form a particle generally referred as exciton. In order for the exciton to relax to the ground state, the energy is given off in the form of photo radiation. The radiation color can be tuned by applying different emitting materials. OLED has been highly-regarded due to a lot of advantages, such as self illumination, wider visual angle (>170°), shorter response time (~μs), higher contrast, higher efficiency, lower power consumption, higher brightness, lower operative voltage (3-10V), thinner size (<2 mm), flexibility and so on.

An exciton generated from recombining a hole and an electron may have triplet state or singlet state for its spin state. The singlet exciton relaxation would radiate fluorescence, and the triplet exciton relaxation would radiate phosphorescence.

In addition, by using a doping method in the emitting layer, self-quenching of the emitting materials can be reduced greatly to enhance the efficiency of the device. Therefore, the search for proper host materials becomes noteworthy since host materials must be capable of capturing carriers and have good energy transfer properties, high glass transition temperature, high thermal stability and appropriate energy gap of the singlet and triplet excited states. However, it would be difficult to search for host materials that fully meet the criteria and there is still some room for host material development in OLED.

Regarding to 9,10-bisphenylphenanthrene derivatives, Japan patent publication No. JP2001-332384A disclosed a 3,6,9,10-tetraphenylphenanthrene having a chemical formula listed below; however, the disclosed 3,6,9,10-tetraphenylphenanthrene still requires improvement in lighting efficiency and thermal stability aspects.

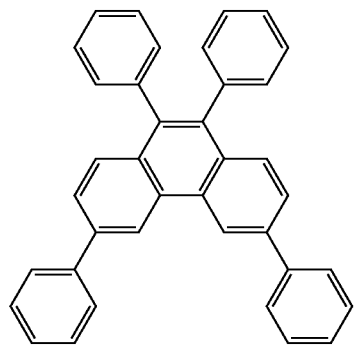

3,6,9,10-tetraphenylphenanthrene

To sum up, it is now a current goal to develop novel host emitters.

SUMMARY OF THE INVENTION

The present invention is directed to 9,10-bisphenylphenanthrene derivatives and organic light emitting diode using the same.

According to one embodiment, a 9,10-bisphenylphenanthrene derivative has a structure of formula (1):

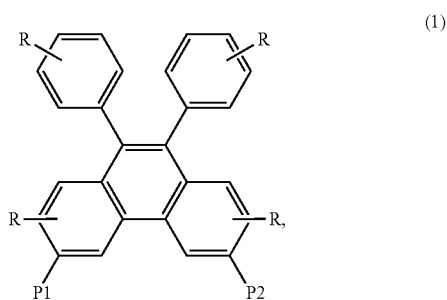

wherein P1 and P2 are substituted or non-substituted polycyclic aromatic hydrocarbons (PAH), and R is a member selected from the group consisting of H, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

According to another embodiment, an organic light emitting diode includes a cathode, an anode and an emitting layer. The emitting layer is configured between the cathode and the anode and includes the aforementioned 9,10-bisphenylphenanthrene derivative.

Other advantages of the present invention will become apparent from the following descriptions taken in conjunction with the accompanying drawings wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed descriptions, when taken in conjunction with the accompanying drawings, wherein.

DESCRIPTION OF THE PREFERRED EMBODIMENT

Figure 1:
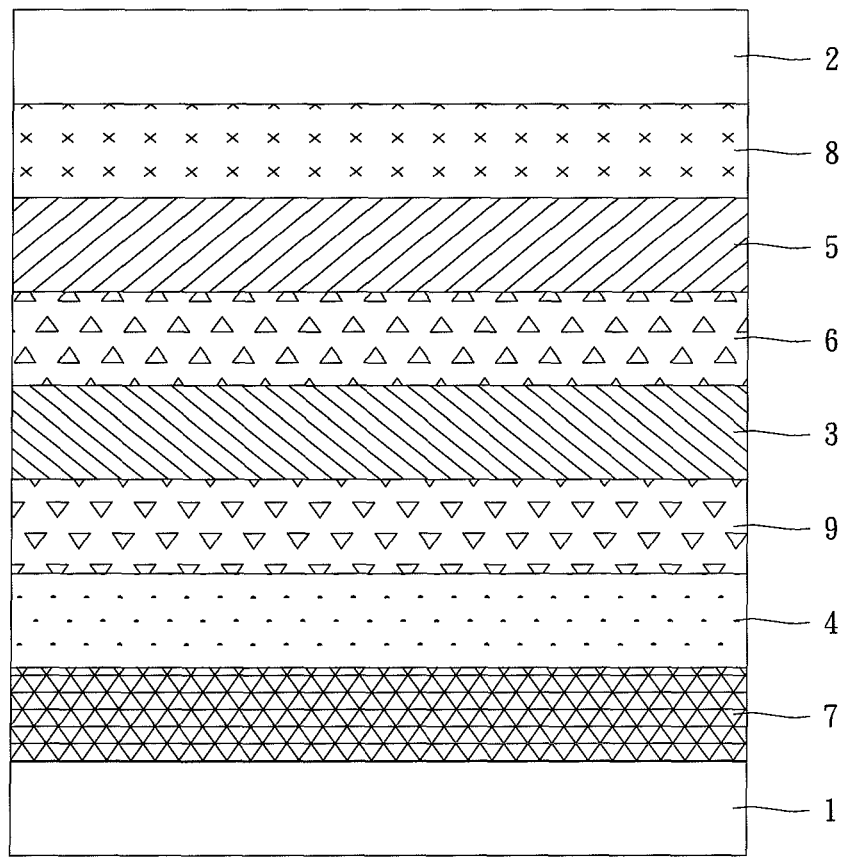
FIGS. 1-3 are schematic diagrams illustrating OLED configuration containing 9,10-bisphenylphenanthrene derivatives of the present invention.

The present invention is directed to 9,10-bisphenylphenanthrene derivatives having a structure of formula (1),

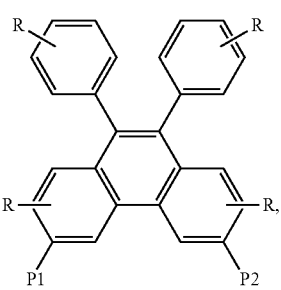

(1)

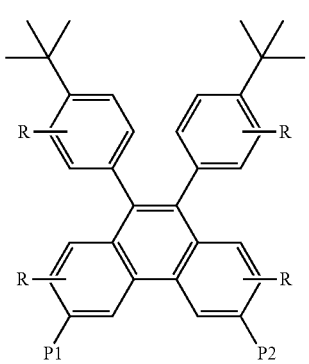

(2)

wherein P1 and P2 are substituted or non-substituted polycyclic aromatic hydrocarbons (PAH). PAHs may include, but not limited to anthracene, benzo[a]pyrane, chrysene, coronene, corannulene, tetracene, naphthalene, pentacene, phenanthrene, pyrene, triphenylene and ovalene. Preferably, PAHs in the 9,10-bisphenylphenanthrene derivatives may be naphthalene, anthracene or pyrene.

Also, P1 and P2 may be the same in one preferred embodiment.

R may be a member selected from the group consisting of H, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

The term "aryl" refers to a hydrocarbon moiety having one or more aromatic rings. Examples of aryl moieties include phenyl (Ph), phenylene, naphthyl, naphthylene, pyrenyl, anthryl, and phenanthryl.

The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, cycloalkyl, cycloalkenyl, heterocycloalkyl, heterocycloalkenyl, aryl and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

In one preferred embodiment, the 9,10-bisphenylphenanthrene derivatives have a structure of formula (2)

The compounds of the present invention have a core phenanthrene structure so as to achieve good thermal stability in devices. In addition, the t-butyl substituent in the compound of formula (2) may contribute to steric effect and prevent from self-quenching effect.

Compound Synthesis

Refer to following reaction scheme illustrating the preparation steps for the 9,10-bisphenylphenanthrene derivatives of the present invention.

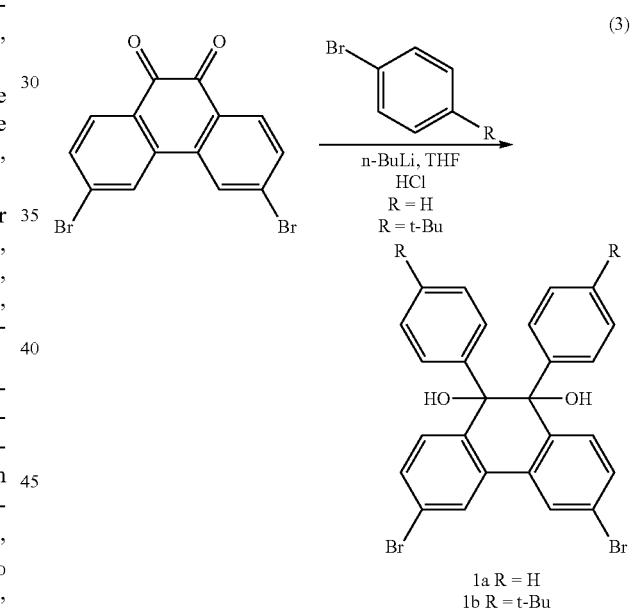

(3)

1a R = H
1b R = t-Bu n-Butyllithium in hexane (2.5M, 16.8 mL) was added slowly under nitrogen to a stirred solution of bromobenzene or 1-bromo-4-tert-butylbenzene (8.52 g, 40.0 mmole) in anhydrous THF (60 mL) at −78° C. The stirring was continued in −78° C. for 30 min and then a solution of 3,6-dibromophenanthrene-9,10-dione (3.66 g, 10.0 mmole) in anhydrous THF (100 mL) was added dropwise. Gradually, the color of the reaction mixture changed to deep green. This mixture was warmed to room temperature and stirred overnight. Thereafter, the reaction mixture was quenched with aqueous HCl (2.0M, 10 mL) and extracted with $CH_2Cl_2$ (2×50 mL). The combined organic phases were dried ($MgSO_4$) and concentrated under reduced pressure. The residue was purified through column chromatography ($SiO_2$; $CH_2Cl_2$/Hexanes 1:4) to yield 1b (2.85 g) as white solid (1a, 1b: 62%, 45%, respectively).

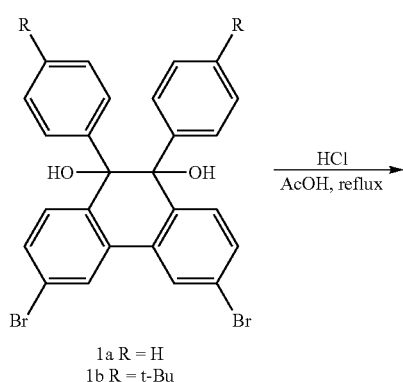

1a R = H
1b R = t-Bu (4) → HCl / AcOH, reflux

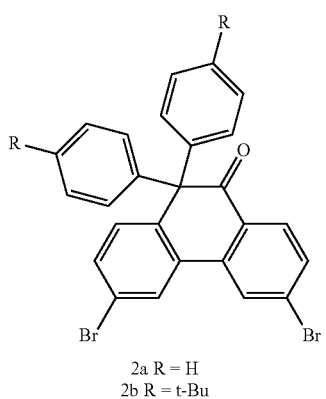

2a R = H
2b R = t-Bu

The solution of HCl (12M, 11.0 mL) in AcOH (25 mL) was added dropwise to a solution 1a or 1b (16.03 g, 25.27 mmol) in AcOH (75.0 mL). Then the mixture was heated under reflux. The resultant solution was refluxed for 30 min and poured into cold water. The mixture was extracted with $CH_2Cl_2$ (100 mL). The combined organic layers were washed with $H_2O$ (100 mL×2), saturated $NaHCO_3$ (100 mL×2) aqueous solution and dried with anhydrous $MgSO_4$. The crude product was purified through column chromatography ($SiO_2$; $CH_2Cl_2$/Hexanes 1:6) to yield 2b (13.61 g) as white solid (2a, 2b: 92%, 87%, respectively).

(5)

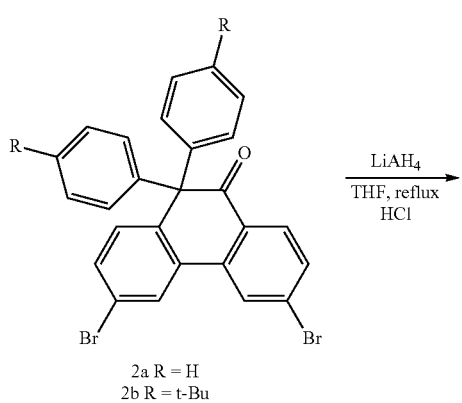

2a R = H
2b R = t-Bu

→ LiAlH₄ / THF, reflux / HCl

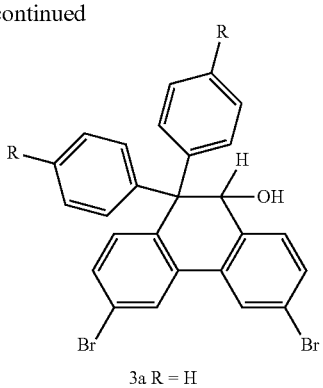

3a R = H
3b R = t-Bu

After degassing, 2a or 2b (13.61 g, 22.08 mmol), anhydrous THF (100 mL) and LiAlH₄ (1.48 g, 38.86 mmol) were added under flow of nitrogen, and then the mixture was heated under reflux while stirring under nitrogen. After 2 h, the reaction mixture was warmed to room temperature. The reaction mixture was quenched with dilute HCl (2.0M, 10 mL) in an ice bath and then extracted with $CH_2Cl_2$ (2×50 mL). The combined organic phases were dried ($MgSO_4$) and concentrated under reduced pressure. The residue was purified through recrystallization to yield 3b (13.61 g) as white solid (3a, 3b: 95%, 97%, respectively).

(6)

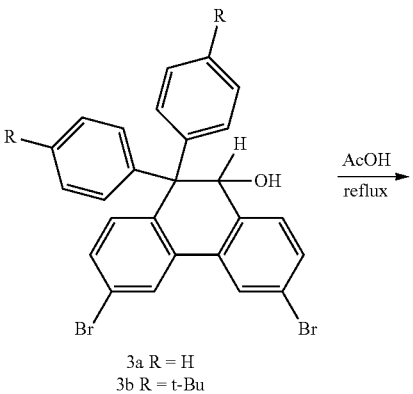

3a R = H
3b R = t-Bu

→ AcOH, reflux

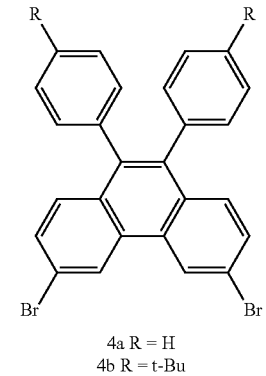

4a R = H
4b R = t-Bu

The product 3a or 3b (3.3 g, 5.34 mmol) was dissolved in a 0.5% acetic acid solution of iodine (60 mL) and reflux for 2 h under flow of nitrogen. The reaction mixture was cooled and then extracted with $CH_2Cl_2$ (100 mL). The combined organic layers were washed with $H_2O$ (100 ml×2), saturated $NaHCO_3$ (100 ml×2) aqueous solution and dried with anhydrous MgSO$_4$. The crude product was purified through column chromatography (SiO$_2$; Hexanes) to yield 4b (3.1 g) as white solid (4a, 4b: 97%, respectively).

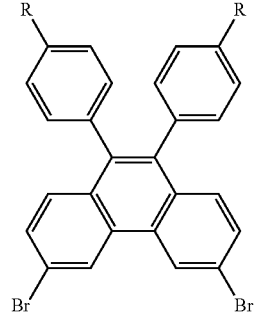

4a R = H
4b R = t-Bu

Suzuki coupling
Ar$_2$B(OR$_1$)$_2$
R = H or alkyl

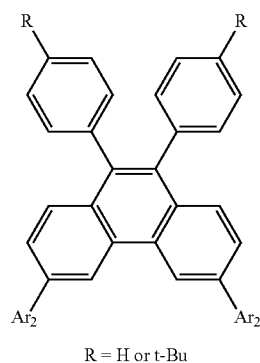

R = H or t-Bu

The product 4a, 4b then may undergo Suzuki coupling reaction illustrated in Formula 7 with arylboronic acids or boronic esters having Ar$_2$, such as benzene, naphthalene, anthracene or pyrane.

Example 1

Reference Compound

TPhP (9,10-bis(4-tert-butylphenyl)-3,6-diphenylphenanthrene)

As shown in Formula 7, the product 4b in Formula 6 (100 mg, 0.17 mmol), phenylboronic acid (52.4 mg, 2.5 mmol), potassium carbonate solution (2.0 M, 4.0 mL), and dried toluene (12 mL) were charged in a two-necked bottle. The bottle was deoxygenated and purged with nitrogen, and the mixture in the bottle was stirred at 60° C. until it was totally dissolved. The nitrogen pressure of the bottle was increased, and Pd(PPh$_3$)$_4$ (20 mg, 0.02 mmol) was rapidly added into the bottle. The reaction was heated to 110° C., and stirred for 48 hours. The reaction mixture was cooled to room temperature, filtered to remove metal and then extracted with CH$_2$Cl$_2$. The combined organic layers were washed with H$_2$O, dried with anhydrous MgSO$_4$, filtered and condensed with reduced pressure. The crude product was purified through column chromatography (SiO$_2$; CH$_2$Cl$_2$/hexanes, 1:20) and then sublimated at a temperature of 280° C. to obtain TPhP (78 mg, 78%) as a white powder.

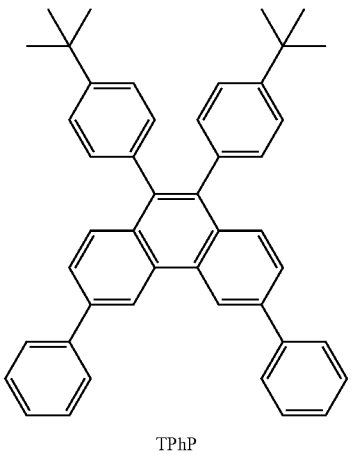

TPhP

The white solid compound in Formula 8 was dissolved in dichloromethane to form a solution having a concentration of 10$^{-5}$M, or evaporated to form a film having a thickness of 30 nm. The absorption-emission peaks of the film and the solution are tabulated (Table 1). Moreover, the HOMO, LUMO and energy gap of TPhP were measured by CV in solution and by ACII in the film (Table 2).

The spectra data of the product in Formula 8 are shown as follows.

$^1$H NMR (400 MHz, CDCl$_3$): δ 9.05 (d, J=1.2 Hz, 2H), 7.81-7.79 (m, 6H), 7.74 (dd, J=1.6, J=8.4 Hz, 2H), 7.53 (t, J=7.6 Hz, 4H), 7.41 (t, J=7.2 Hz, 2H), 7.22 (d, J=8.0 Hz, 4H), 7.06 (d, J=8.4 Hz, 4H), 1.28 (s, 18H).

$^{13}$C NMR (100 MHz, CDCl$_3$): δ 149.1, 141.5, 139.1, 137.5, 136.4, 131.4, 130.7, 130.3, 128.9, 128.6, 127.7, 127.4, 126.0, 124.2, 121.0, 34.4, 31.3

HRMS (m/z): [M$^+$] calcd. for C$_{46}$H$_{42}$, 594.3287. found, 594.3276.

Anal. calcd for C$_{46}$H$_{42}$: C, 92.88; H, 7.12. found: C, 92.82; H, 7.18.

Example 2

TNaP (9,10-bis(4-tert-butylphenyl)-3,6-di(naphthalen-2-yl)phenanthrene)

As illustrated in Formula 7, the product 4b in Formula 6 (500 mg, 0.83 mmol), 2-naphthylboronic acid (428 mg, 2.49 mmol), potassium carbonate solution (2.0 M, 8.0 mL), and dried toluene (24 mL) were charged in a two-necked bottle. The bottle was deoxygenated and purged with nitrogen, and the mixture in the bottle was stirred at 60° C. until it was totally dissolved. The nitrogen pressure of the bottle was increased, and Pd(PPh$_3$)$_4$ (96 mg, 0.08 mmol) was rapidly added into the bottle. The reaction was heated to 110° C., and stirred for 48 hours. The reaction mixture was cooled to room temperature, filtered to remove metal and then extracted with CH$_2$Cl$_2$. The combined organic layers were washed with H$_2$O, dried with anhydrous MgSO$_4$, filtered and condensed with reduced pressure. The crude product was purified through column chromatography (SiO$_2$; CH$_2$Cl$_2$/hexanes, 1:20) and then sublimated at a temperature of 285° C. to obtain TNaP (463 mg, 80%) as a white powder.

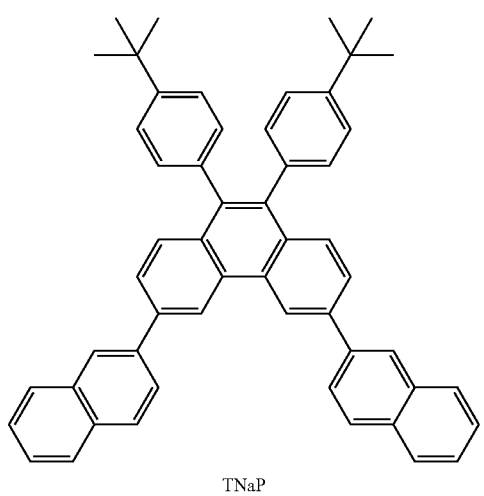

TNaP

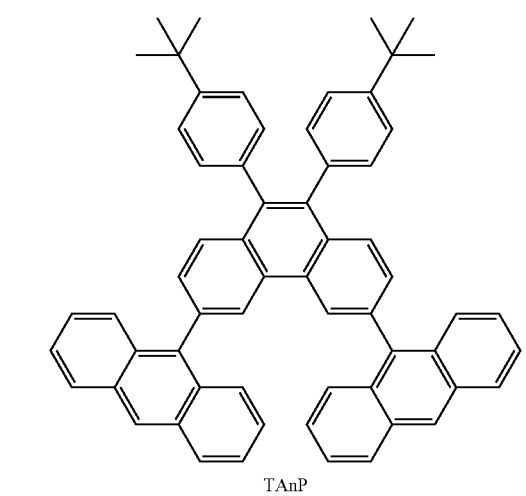

TAnP

The white solid compound in Formula 9 was dissolved in dichloromethane to form a solution having a concentration of $10^{-5}$ M, or evaporated to form a film having a thickness of 30 nm. The absorption-emission peaks of the film and the solution are tabulated (Table 1). Moreover, the HOMO, LUMO and energy gap of TNaP were measured by CV in solution and ACII in the film (Table 2).

The spectra data of the product in Formula 9 are shown as follows.

$^1$H NMR (400 MHz, CDCl$_3$): δ 9.21 (d, J=0.8 Hz, 2H), 8.25 (s, 2H), 8.01-7.95 (m, 6H), 7.92-7.84 (m, 6H), 7.55-7.48 (m, 4H), 7.24 (d, J=8.4 Hz, 4H), 7.09 (d, J=8.4 Hz, 4H), 1.29 (s, 18H).

$^{13}$C NMR (100 MHz, CDCl$_3$): δ 149.1, 139.0, 138.9, 137.6, 136.5, 133.8, 132.7, 131.5, 130.8, 130.4, 128.7, 128.6, 128.3, 127.7, 126.4, 126.3, 126.3, 126.1, 126.0, 124.2, 121.3, 34.4, 31.3.

HRMS (m/z): [M$^+$] calcd. for C$_{54}$H$_{46}$, 694.3600. found, 694.3604.

Anal. calcd for C$_{54}$H$_{46}$: C, 93.33; H, 6.67. found: C, 93.16; H, 6.77.

Example 3

TAnP (9,9'-(9,10-bis(4-tert-butylphenyl)-9,10-dihydrophenanthrene-3,6-diyl)dianthracene)

As illustrated in Formula 7, the product 4b in Formula 6 (1.0 g, 1.67 mmol), anthracen-9-ylboronic acid (1.11 g, 5.0 mmol), potassium carbonate solution (2.0 M, 20 mL), and dried toluene (60 mL) were charged in a two-necked bottle. The bottle was deoxygenated and purged with nitrogen, and the mixture in the bottle was stirred at 60° C. until it was totally dissolved. The nitrogen pressure of the bottle was increased, and Pd(PPh$_3$)$_4$ (196 mg, 0.17 mmol) was rapidly added into the bottle. The reaction was heated to 110° C., and stirred for 48 hours. The reaction mixture was cooled to room temperature, filtered to remove metal and then extracted with CH$_2$Cl$_2$. The combined organic layers were washed with H$_2$O, dried with anhydrous MgSO$_4$, filtered and condensed with reduced pressure. The crude product was purified through column chromatography (SiO$_2$; CH$_2$Cl$_2$/hexanes, 1:5) and then sublimated at a temperature of 300° C. to obtain TAnP (627 mg, 47%) as a pale yellow powder.

The pale yellow solid compound in Formula 10 was dissolved in dichloromethane to form a solution having a concentration of $10^{-5}$ M, or evaporated to form a film having a thickness of 30 nm. The absorption-emission peaks of the film and the solution are tabulated (Table 1). Moreover, the HOMO, LUMO and energy gap of TAnP were measured by CV in solution and ACII in the film (Table 2).

The spectra data of the product in Formula 10 are shown as follows.

$^1$H NMR (400 MHz, CDCl$_3$): δ 8.76 (d, J=1.2 Hz, 2H), 8.44 (s, 2H), 8.00-7.97 (m, 6H), 7.69 (d, J=8.8 Hz, 4H), 7.60 (dd, J=1.2, J=8.4 Hz, 2H), 7.40-7.36 (m, 4H), 7.32-7.24 (m, 12H), 1.31 (s, 18H).

$^{13}$C NMR (100 MHz, CDCl$_3$): δ 149.2, 137.9, 137.0, 136.9, 136.5, 131.5, 131.3, 130.8, 130.4, 130.1, 129.8, 128.3, 128.1, 126.9, 126.6, 125.4, 125.3, 125.0, 124.4, 34.5, 31.3.

HRMS (m/z): [M$^+$] calcd. for C$_{62}$H$_{50}$, 794.3913. found, 794.3922.

Anal. calcd for C$_{62}$H$_{50}$: C, 93.66; H, 6.34. found: C, 93.30; H, 6.34.

Example 4

TAnPP (10,10'-(9,10-bis(4-tert-butylphenyl)-9,10-dihydrophenanthrene-3,6-diyl)bis(9-phenylanthracene))

A compound 9,10-dibromoanthracene (8.00 g, 23.8 mmol), phenylboronic acid (3.19 g, 26.2 mmol), potassium carbonate solution (2.0 M, 20.0 mL), and dried toluene (60 mL) were charged in a two-necked bottle. The two-necked bottle was deoxygenated and purged with nitrogen, and the mixture in the bottle was stirred at 60° C. until it was totally dissolved. The nitrogen pressure of the bottle was increased, and Pd(PPh$_3$)$_4$ (1.38 g, 1.19 mmol) was rapidly added into the bottle. The reaction was heated to 110° C., and stirred for 48 hours. The reaction mixture was cooled to room temperature. The resulting mixture was filtered to remove metal. The filtrate was extracted by the dichloromethane. The organic layer of the extraction was dried by MgSO$_4$, condensed, and purified by chromatography with an eluent of hexanes to obtain a white solid of 3.97 g (yield=50%) as illustrated in Formula II.

(11)

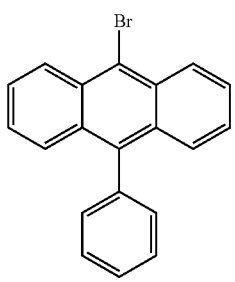

The compound in Formula II (1.50 g, 4.5 mmol) was charged in a reaction bottle. The reaction bottle was then heated, vacuumed, and purged with nitrogen. Dried tetrahydrofuran (24 mL) was added to the reaction bottle and stirred until the compound in Formula II was dissolved, and the solution was cooled to −78° C. n-BuLi (2.16 mL, 5.4 mmol, 2.5 M n-hexane solution) was dropwise added to the cooled solution, and the reaction was stirred at −78° C. for 1 hour. Subsequently, B(OCH$_3$)$_3$ (0.78 mL, 6.8 mmol) was added to the reaction for reaction for another 8 hours. The resulting mixture was extracted by ethyl ether and water. The organic layer of the extraction was dried by MgSO$_4$, and condensed to obtain a solid. The solid was charged in a reaction bottle. Benzene (15 mL) and pinacol (1.07 g, 9.1 mmol) were added to the reaction bottle. The mixture was heated to 110° C. to reflux for 2 hours. The resulting mixture was directly condensed, and purified by chromatography with an eluent of hexanes to obtain a white solid of 1.00 g (yield=58%) as illustrated in Formula 12.

(12)

As illustrated in Formula 7, the product 4b in Formula 6 (1.0 g, 1.67 mmol), the compound in Formula 12 (1.91 g, 5.0 mmol), potassium carbonate solution (2.0 M, 20 mL), and dried toluene (60 mL) were charged in a two-necked bottle. The bottle was deoxygenated and purged with nitrogen, and the mixture in the bottle was stirred at 60° C. until it was totally dissolved. The nitrogen pressure of the bottle was increased, and Pd(PPh$_3$)$_4$ (196 mg, 0.17 mmol) was rapidly added into the bottle. The reaction was heated to 110° C., and stirred for 48 hours. The reaction mixture was cooled to room temperature, filtered to remove metal and then extracted with CH$_2$Cl$_2$. The combined organic layers were washed with H$_2$O, dried with anhydrous MgSO$_4$, filtered and condensed with reduced pressure. The crude product was purified through column chromatography (SiO$_2$; CH$_2$Cl$_2$/hexanes, 1:5) and then sublimated at a temperature of 380° C. to obtain TAnPP (743 mg, 47%) as yellow powder.

(13)

TAnPP

The yellow powder compound in Formula 13 was dissolved in dichloromethane to form a solution having a concentration of $10^{-5}$ M, or evaporated to form a film having a thickness of 30 nm. The absorption-emission peaks of the film and the solution are tabulated (Table 1). Moreover, the HOMO, LUMO and energy gap of TAnPP were measured by CV in solution and ACII in the film (Table 2).

The spectra data of the product in Formula 13 are shown as follows.

$^1$H NMR (400 MHz, CDCl$_3$): δ 8.82 (d, J=1.2 Hz, 2H), 7.93 (d, J=8.4 Hz, 2H), 7.75-7.73 (m, 4H), 7.67-7.53 (m, 12H), 7.45 (d, J=7.6 Hz, 2H), 7.39-7.37 (m, 6H), 7.31-7.26 (m, 12H), 1.34 (s, 18H).

HRMS (m/z): [M$^+$] calcd. for C$_{74}$H$_{58}$, 946.4539. found, 946.4529.

Anal. calcd for C$_{74}$H$_{58}$: C, 93.83; H, 6.17. found: C, 93.79; H, 6.20.

Example 5

TPP (9,10-bis(4-tert-butylphenyl)-3,6-di(pyrene-1-yl)phenanthrene)

As illustrated in Formula 7, the product 4b in Formula 6 (500 mg, 0.83 mmol), 1-pyreneboronic acid (613 mg, 2.5 mmol), potassium carbonate solution (2.0 M, 10 mL), and dried toluene (30 mL) were charged in a two-necked bottle. The bottle was deoxygenated and purged with nitrogen, and the mixture in the bottle was stirred at 60° C. until it was totally dissolved. The nitrogen pressure of the bottle was increased, and Pd(PPh$_3$)$_4$ (96 mg, 0.08 mmol) was rapidly added into the bottle. The reaction was heated to 110° C., and stirred for 48 hours. The resulting mixture was cooled to room temperature to precipitate a solid, and the solid was collected by filtering. The solid was sublimated at a temperature of 330° C. to obtain a white solid of 518 mg (yield=74%).

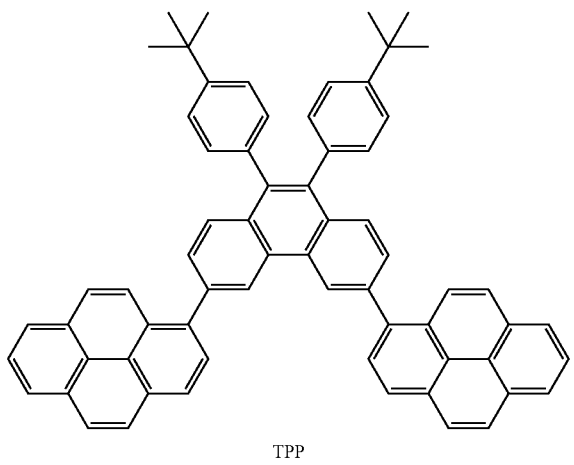

(14)

TPP

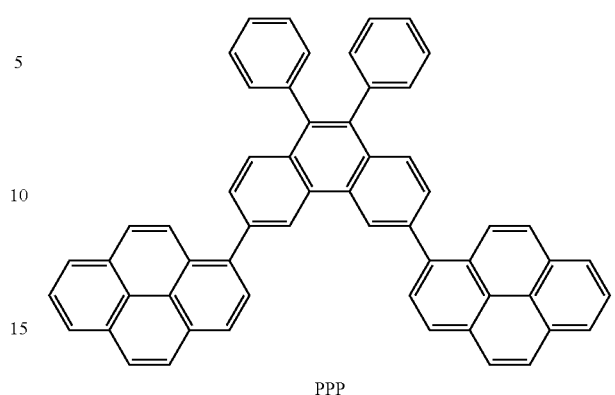

(15)

PPP

The white solid compound in Formula 14 was dissolved in dichloromethane to form a solution having a concentration of $10^{-5}$ M, or evaporated to form a film having a thickness of 30 nm. The absorption-emission peaks of the film and the solution are tabulated (Table 1). Moreover, the HOMO, LUMO and energy gap of TPP were measured by CV in solution and ACII in the film (Table 2).

The spectra data of the product in Formula 14 are shown as follows.

$^1$H NMR (400 MHz, CDCl$_3$): δ 9.08 (d, J=1.6 Hz, 2H), 8.26 (d, J=9.2 Hz, 2H), 8.21 (d, J=8.0 Hz, 2H), 8.15 (d, J=8.0 Hz, 2H), 8.10 (d, J=8.0 Hz, 4H), 8.06 (s, 4H), 7.99-7.95 (m, 6H), 7.82 (dd, J=1.4, J=8.2 Hz, 2H), 7.29 (d, J=8.4 Hz, 4H), 7.20 (d, J=8.4 Hz, 4H), 1.30 (s, 18H).

$^{13}$C NMR (100 MHz, CDCl$_3$): δ 149.2, 139.2, 137.8, 136.5, 131.5, 131.4, 130.9, 130.8, 130.7, 130.0, 129.4, 128.7, 128.0, 127.9, 127.7, 127.5, 127.4, 126.0, 125.3, 125.1, 125.0, 124.8, 124.8, 124.7, 124.5, 124.3, 34.5, 31.3.

HRMS (m/z): [M$^+$] calcd. for C$_{66}$H$_{50}$, 842.3913. found, 842.3926.

Anal. calcd for C$_{66}$H$_{50}$: C, 94.02; H, 5.98. found: C, 94.01; H, 5.96.

Example 6

PPP (9,10-diphenyl-9,10-dihydrophenanthrene-3,6-diyl)dipyrene)

As illustrated in Formula 7, the product 4a in Formula 6 (1.0 g, 2.05 mmol), 1-pyreneboronic acid (1.53 g, 6.2 mmol), potassium carbonate solution (2.0 M, 10 mL), and dried toluene (30 mL) were charged in a two-necked bottle. The bottle was deoxygenated and purged with nitrogen, and the mixture in the bottle was stirred at 60° C. until it was totally dissolved. The nitrogen pressure of the bottle was increased, and Pd(PPh$_3$)$_4$ (243 mg, 0.21 mmol) was rapidly added into the bottle. The reaction was heated to 110° C., and stirred for 48 hours. The resulting mixture was cooled to room temperature to precipitate a solid, and the solid was collected by filtering. The solid was sublimated at a temperature of 330° C. to obtain a white solid of 1.03 g (yield=69%).

The white solid compound in Formula 15 was dissolved in dichloromethane to form a solution having a concentration of $10^{-5}$ M, or evaporated to form a film having a thickness of 30 nm. The absorption-emission peaks of the film and the solution are tabulated (Table 1). Moreover, the HOMO, LUMO and energy gap of PPP were measured by CV in solution and ACII in the film (Table 2).

The spectra data of the product in Formula 15 are shown as follows.

$^1$H NMR (400 MHz, CD$_2$Cl$_2$): δ 9.12 (d, J=1.6 Hz, 2H), 8.28-8.24 (m, 4H), 8.20 (d, J=7.6 Hz, 2H), 8.15-8.13 (m, 4H), 8.10 (s, 4H), 8.04-7.98 (m, 4H), 7.83 (dd, J=1.6, J=8.4 Hz, 2H), 7.77 (d, J=8.4 Hz, 2H), 7.37-7.27 (m, 10H).

$^{13}$C NMR (100 MHz, CD$_2$Cl$_2$): δ 140.0, 139.7, 138.0, 137.7, 131.8, 131.8, 131.5, 131.3, 131.1, 130.5, 129.9, 129.0, 128.3, 128.2, 128.1, 128.1, 127.8, 127.7, 127.0, 126.5, 125.5, 125.5, 125.2, 125.1, 125.1, 125.0.

HRMS (m/z): [M$^+$] calcd. for C$_{58}$H$_{34}$, 730.2661. found, 730.2662.

Anal. calcd for C$_{58}$H$_{34}$: C, 95.31; H, 4.69. found: C, 95.28; H, 4.76.

Example 7

PTP (6,6'-(9,10-diphenyl-9,10-dihydrophenanthrene-3,6-diyl)bis(2-tert-butylpyrene))

As illustrated in Formula 7, the product 4a in Formula 6 (1.2 g, 2.46 mmol), 7-tert-butylpyren-1-ylboronic acid (2.23 g, 7.38 mmol), potassium carbonate solution (2.0 M, 10 mL), and dried toluene (30 mL) were charged in a two-necked bottle. The bottle was deoxygenated and purged with nitrogen, and the mixture in the bottle was stirred at 60° C. until it was totally dissolved. The nitrogen pressure of the bottle was increased, and Pd(PPh$_3$)$_4$ (289 mg, 0.25 mmol) was rapidly added into the bottle. The reaction was heated to 110° C., and stirred for 48 hours. The resulting was cooled to room temperature to precipitate a solid, and the solid was collected by filtering. The solid was sublimated at a temperature of 330° C. to obtain a white solid of 1.56 g (yield=75%).

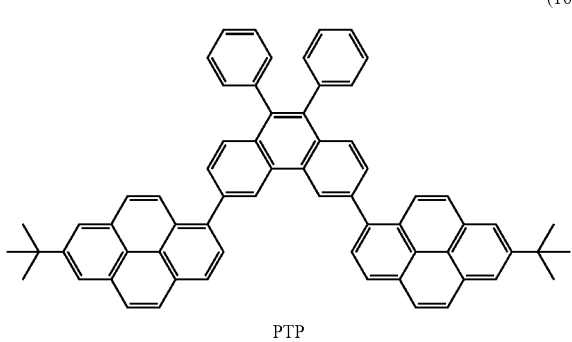

PTP
(16)

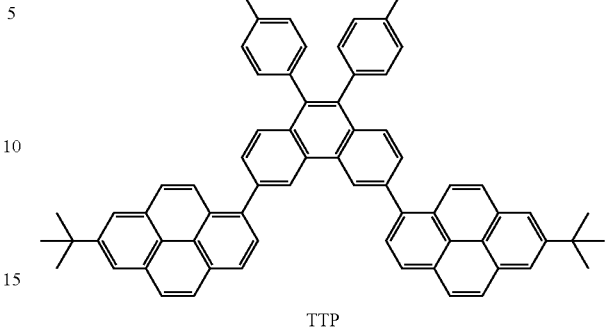

TTP
(17)

The white solid compound in Formula 16 was dissolved in dichloromethane to form a solution having a concentration of $10^{-5}$ M, or evaporated to form a film having a thickness of 30 nm. The absorption-emission peaks of the film and the solution are tabulated (Table 1). Moreover, the HOMO, LUMO and energy gap of PTP were measured by CV in solution and ACII in the film (Table 2).

The spectra data of the product in Formula 16 are shown as follows.

$^1$H NMR (400 MHz, CD$_2$Cl$_2$): δ 9.12 (d, J=1.6 Hz, 2H), 8.25-8.19 (m, 8H), 8.10 (d, J=8.0 Hz, 2H), 8.07 (s, 4H), 8.00 (d, J=9.6 Hz, 2H), 7.83 (dd, J=1.6, J=8.4 Hz, 2H), 7.76 (d, J=8.4 Hz, 2H), 7.36-7.35 (m, 8H), 7.32-7.27 (m, 2H), 1.55 (s, 18H).

$^{13}$C NMR (100 MHz, CD$_2$Cl$_2$): δ 149.7, 140.1, 139.8, 137.8, 137.7, 131.7, 131.7, 131.5, 131.1, 130.9, 130.5, 129.9, 128.8, 128.3, 128.2, 128.1, 128.0, 128.0, 127.5, 127.0, 125.3, 125.2, 124.9, 124.8, 123.3, 122.9, 122.6, 35.5, 32.0.

HRMS (m/z): calcd. for C$_{66}$H$_{50}$, 842.3913. found, 842.3900.

Anal. calcd for C$_{66}$H$_{50}$: C, 94.02; H, 5.98. found: C, 94.02; H, 5.95.

Example 8

TTP (6,6'-(9,10-bis(4-tert-butylphenyl)-9,10-dihydrophenanthrene-3,6-diyl)bis(2-tert-butylpyrene))

As illustrated in Formula 7, the product 4b in Formula 6 (1.0 g, 1.67 mmol), 7-tert-butylpyren-1-ylboronic acid (1.52 g, 5.01 mmol), potassium carbonate solution (2.0 M, 10 mL), and dried toluene (30 mL) were charged in a two-necked bottle. The bottle was deoxygenated and purged with nitrogen, and the mixture in the bottle was stirred at 60° C. until it was totally dissolved. The nitrogen pressure of the bottle was increased, and Pd(PPh$_3$)$_4$ (196 mg, 0.17 mmol) was rapidly added into the bottle. The reaction was heated to 110° C., and stirred for 48 hours. The resulting mixture was cooled to room temperature to precipitate a solid, and the solid was collected by filtering. The solid was sublimated at a temperature of 425° C. to obtain a white solid of 1.3 g (yield=78%).

The white solid compound in Formula 17 was dissolved in dichloromethane to form a solution having a concentration of $10^{-5}$ M, or evaporated to form a film having a thickness of 30 nm. The absorption-emission peaks of the film and the solution are tabulated (Table 1). Moreover, the HOMO, LUMO and energy gap of TTP were measured by CV in solution and ACII in the film (Table 2).

The spectra data of the product in Formula 17 are shown as follows.

$^1$H NMR (400 MHz, CDCl$_3$): δ 9.08 (d, J=1.2 Hz, 2H), 8.23 (d, J=9.2 Hz, 2H), 8.19-8.17 (m, 4H), 8.14 (d, J=1.6 Hz, 2H), 8.07 (d, J=8.0 Hz, 2H), 8.03 (s, 4H), 7.97-7.94 (m, 4H), 7.82 (dd, J=1.2, J=8.2 Hz, 2H), 7.29 (d, J=8.4 Hz, 4H), 7.20 (d, J=8.4 Hz, 4H), 1.54 (s, 18H), 1.31 (s, 18H).

$^{13}$C NMR (100 MHz, CDCl$_3$): δ 149.2, 149.1, 139.4, 137.8, 137.6, 136.6, 131.3, 130.9, 130.5, 130.1, 129.4, 128.5, 128.0, 127.9, 127.6, 127.5, 127.2, 125.1, 124.9, 124.5, 124.3, 123.1, 122.4, 122.1, 35.2, 34.5, 31.9, 31.4.

HRMS (m/z): [M$^+$] calcd. for C$_{74}$H$_{66}$, 954.5165. found, 954.5164.

Anal. calcd for C$_{74}$H$_{66}$: C, 93.04; H, 6.96. found: C, 93.08; H, 7.02.

Luminescence Properties of 9,10-bisphenylphenanthrene Derivatives

Referring to Table 1, the emitting length for 9,10-bisphenylphenanthrene derivatives ranges from 380 to 506 nm and matches blue light. Also, it is noted that TPP has a good quantum yield in thin film (0.83).

TABLE 1

Luminescence properties of 9,10-bisphenylphenanthrene derivatives

| Compound | λabs in DCM (nm) | λem in DCM (nm) | λabs (thin fim) (nm) | λem in (thin film) (nm) | Q.Y. (thin film) (nm) |
|---|---|---|---|---|---|
| TPhP (Reference) | 272, 328 | 380, 395 | 274, 336 | 397 | 0.57 |
| TNaP | 268, 338 | 395, 406 | 272, 348 | 418 | 0.64 |
| TAnP | 256, 350, 368, 388 | 418, 431 | 263, 356, 374, 393 | 454, 488 | — |
| TAnPP | 259, 358, 376, 397 | 430 | 266, 365, 382, 402 | 447, 506 | — |
| TPP | 242, 282, 346 | 424 | 246, 286, 358 | 460 | 0.83 |
| PPP | 242, 282, 348 | 418 | 247, 286, 359 | 462 | — |
| PTP | 246, 284, 350 | 418 | 249, 288, 358 | 454 | — |
| TTP | 246, 284, 350 | 422 | 249, 288, 357 | 448 | — |

As shown in Table 1, in comparison to the control compound TPhP, the 9,10-bisphenylphenanthrene derivatives of the present invention have shown better quantum yield in thin film, particularly TPP (0.83).

TABLE 2

Energy Gap Level for 9,10-bisphenylphenanthrene derivatives

|  | TPhP | TNaP | TAnP | TAnPP | TPP | PPP | PTP | TTP |
|---|---|---|---|---|---|---|---|---|
| HOMO(eV)[a] | 5.79 | 5.61 | 5.58 | 5.62 | 5.56 | 5.61 | 5.59 | 5.60 |
| HOMO(eV)[b] | 5.77 | 5.72 | 5.67 | 5.60 | 5.60 | 5.55 | 5.63 | 5.62 |
| LUMO(eV)[b] | 2.36 | 2.36 | 2.51 | 2.63 | 2.45 | 2.50 | 2.48 | 2.49 |
| Eg(eV) | 3.43 | 3.25 | 3.07 | 2.99 | 3.11 | 3.11 | 3.11 | 3.11 |

[a] measured by ACII in the film
[b] measured by CV in solution.

Thermal Stability of 9,10-bisphenylphenanthrene Derivatives

Referring to Table 3, the 9,10-bisphenylphenanthrene derivatives have better thermal stability ($T_g$: 197~230° C.; $T_d$: 484° C.~504° C.) in comparison to TPhP.

TABLE 3

Thermal stability of 9,10-bisphenylphenanthrene derivatives

|  | TPhP | TNaP | TAnP | TAnPP | TPP | PPP | PTP | TTP |
|---|---|---|---|---|---|---|---|---|
| $T_g$ (° C.) | N.D. | 134 | N.D. | N.D. | 211 | 197 | 226 | 230 |
| $T_m$ (° C.) | N.D. | 291 | N.D. | N.D. | 378 | N.D. | N.D. | N.D. |
| $T_d$ (° C.) | 367 | 438 | 454 | 485 | 504 | 484 | 502 | 496 |

$T_g$: glass transition temperature; $T_d$: decomposition temperature; N.D.: Not detected.

OLED Configuration

Refer to FIG. 1, which is a schematic diagram illustrating an organic light emitting device containing 9,10-bisphenylphenanthrene derivatives according to one embodiment of the present invention. The light emitting device includes an emitting layer 3 configured between an anode 1 and a cathode 2. The emitting layer 3 is made of host emitting material doped with light emitting material. The light emitting device may also include a hole injecting layer 7, a hole transport layer 4, an electron blocking layer 9, an emitting layer 3, a hole blocking layer 6, an electron transport layer 5 and an electron injecting layer 8 sequentially configured on top of the anode 1. The real thickness of each layer doesn't correspond to the schematic size, and electron blocking layer 9, hole blocking layer 6 and electron injecting layer 8 may be optional. The 9,10-bisphenylphenanthrene derivatives of the present invention may be used as a host emitter or a dopant in the light emitting layer.

Example 9

Configuration of Undoped OLED

Figure 2:
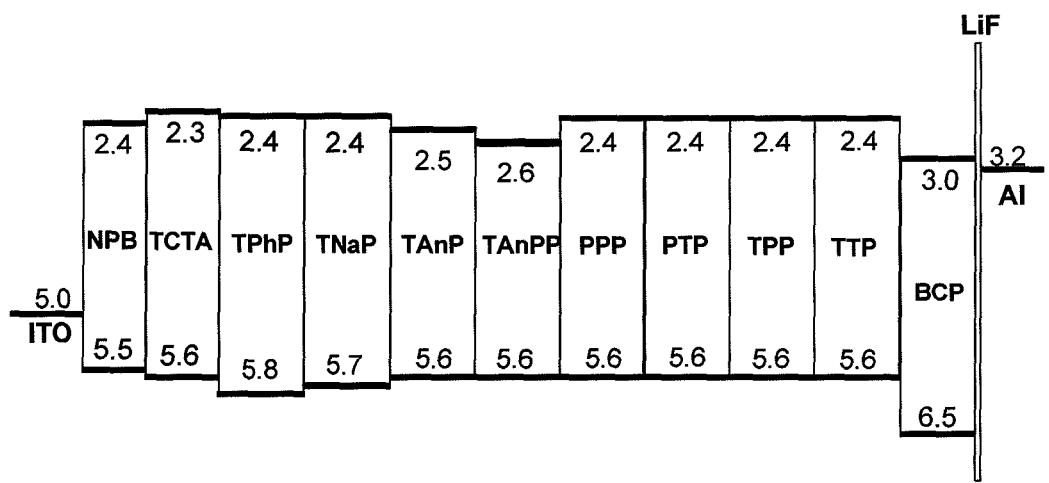

Refer to FIG. 2, which illustrates a device structure of an undoped OLED, where ITO is used for a substrate and an electrode; the tested electrode includes LiF/Al; the tested hole transport layer includes NPB (4,4'-bis[N-(1-naphthyl)-N-phenyl-amino]biphenyl) and TCTA (4,4',4"-tri(N-carbazolyl)triphenylamine), which also can be used for electron blocking material, or electron blocking material and hole transporting material simultaneously; the tested electron transport layer includes BCP (2,9-dimethyl-4,7-diphenyl-[1, 10]-phenanthroline), which can be used for hole blocking layer or hole blocking layer and electron transport layer simultaneously. The 9,10-bisphenylphenanthrene derivatives of the present invention are used for host emitting material in the emitting layer. The HOMO and LUMO data of each device is also illustrated in the figure.

The detailed configuration and width (nm) of the tested devices are respectively illustrated as follows, and the measured performance is listed in Table 4.

Device A: NPB(20)/TCTA (30)/TPhP(40)/BCP(30)/LiF (1)/Al(100)
Device B: NPB(20)/TCTA (30)/TNaP(40)/BCP(30)/LiF (1)/Al(100)
Device C: NPB(20)/TCTA (30)/TPP(40)/BCP(30)/LiF(1)/Al(100)
Device D: TCTA (50)/PPP(40)/BCP(30)/LiF(1)/Al(100)
Device E: TCTA (50)/PTP(40)/BCP(30)/LiF(1)/Al(100)
Device F: TCTA (50)/TPP(40)/BCP(30)/LiF(1)/Al(100)
Device G: TCTA (50)/TTP(40)/BCP(30)/LiF(1)/Al(100)

TABLE 4

Performance of undoped OLEDs containing the 9,10-bisphenylphenanthrene derivatives of the present invention

| Device | host | E.Q.E. (%)(V) | C.E. (cd/A) | P.E. (lm/W) | Max. Brightness (V) | Vd (V) | EL λmax (nm) | FWHM (nm) | CIE(x, y) |
|---|---|---|---|---|---|---|---|---|---|
| A | TPhP | 1.3(5.0) | 0.3 | 0.2 | 626(13.0) | 4.0 | 410 | 59 | (0.16, 0.04) |
| B | TNaP | 1.2(7.5) | 0.3 | 0.2 | 1189(12.0) | 3.7 | 418 | 57 | (0.16, 0.04) |
| C | TPP | 4.1(7.0) | 5.2 | 3.2 | 18134(12.5) | 3.2 | 460 | 78 | (0.15, 0.15) |
| D | PPP | 5.31(7.0) | 6.8 | 3.1 | 20870(15.0) | 4.2 | 460 | 66 | (0.16, 0.15) |
| E | PTP | 6.15(8.5) | 5.9 | 3.1 | 22132(15.5) | 3.3 | 450 | 70 | (0.15, 0.11) |
| F | TPP | 5.03(9.5) | 6.4 | 2.7 | 23897(16.5) | 3.6 | 460 | 76 | (0.15, 0.15) |
| G | TTP | 6.36(8.5) | 8.0 | 6.1 | 27189(15.5) | 3.0 | 477 | 83 | (0.15, 0.16) |

Example 10

Configuration of Doped OLED

Figure 3:
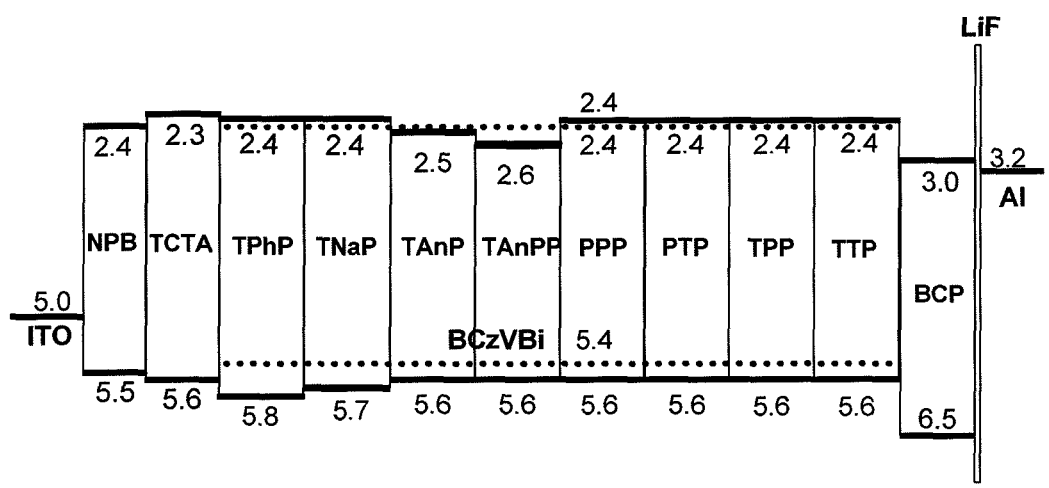

Refer to FIG. 3, which illustrates a device structure of a doped OLED, where ITO is used for a substrate and an electrode; the tested electrode includes LiF/Al; the host emitting layer contains the example compounds of the present invention as the host emitter and is doped with 5% BczVBi(4,4'-bis(9-ethyl-3-carbazovinylene)-1,1'-biphenyl); the tested hole transport layer includes TCTA; and the tested electron transport layer includes BCP. In addition, a control group includes DPVBi(1,4-bis(2,2-diphenylvinyl)biphenyl) as the reference host emitter.

The detailed configuration and width (nm) of the tested devices are respectively illustrated as follows, and the measured performance is listed in Table 5.

IA: NPB(20)/TCTA(30)/TPhP:BCzVBi(5%)(40)/BCP(30)/LiF(1)/Al(100)
IB: NPB(20)/TCTA(30)/TNaP:BCzVBi(5%)(40)/BCP(30)/LiF(1)/Al(100)
IC: NPB(20)/TCTA(30)/TPP:BCzVBi(5%)(40)/BCP(30)/LiF(1)/Al(100)
ID: TCTA(50)/PPP:BCzVBi(5%)(40)/BCP(30)/LiF(1)/Al(100)
IE: TCTA(50)/PTP:BCzVBi(5%)(40)/BCP(30)/LiF(1)/Al(100)
IF: TCTA(50)/TPP:BCzVBi(5%)(40)/BCP(30)/LiF(1)/Al(100)
IG: TCTA(50)/TTP:BCzVBi(5%)(40)/BCP(30)/LiF(1)/Al(100)
IH: TCTA(50)/DPVBi:BCzVBi(5%)(40)/BCP(30)/LiF(1)/Al(100)

TABLE 5

Performance of doped OLEDs containing the 9,10-bisphenylphenanthrene derivatives of the present invention

| Device | host | E.Q.E. (%)(V) | C.E. (cd/A) | P.E. (lm/W) | Max. Brightness (V) | Vd (V) | EL λmax (nm) | FWHM (nm) | CIE(x, y) |
|---|---|---|---|---|---|---|---|---|---|
| IA | TPhP/BCzVBi | 5.2(5.5) | 5.0 | 3.2 | 8641(16.5) | 3.8 | 444 | 56 | (0.14, 0.10) |
| IB | TNaP/BCzVBi | 5.6(5.0) | 6.5 | 4.6 | 14912(16.0) | 3.6 | 449 | 61 | (0.14, 0.13) |
| IC | TPP/BCzVBi | 6.4(9.0) | 7.7 | 5.1 | 27762(15.0) | 3.6 | 450 | 62 | (0.14, 0.14) |
| ID | PPP/BCzVBi | 7.40(8.0) | 10.2 | 5.3 | 41881(17.0) | 3.2 | 453 | 60 | (0.15, 0.16) |
| IE | PTP/BCzVBi | 8.18(8.5) | 7.5 | 4.5 | 31202(16.5) | 3.1 | 448 | 51 | (0.14, 0.10) |
| IF | TPP/BCzVBi | 6.41(7.5) | 6.9 | 4.1 | 30480(18.0) | 3.1 | 450 | 54 | (0.14, 0.12) |
| IG | TTP/BCzVBi | 7.28(7.5) | 6.9 | 4.5 | 29060(17.5) | 3.1 | 445 | 54 | (0.15, 0.10) |
| IH | DPVBi/BCzVBi | 5.88(10.0) | 6.5 | 2.2 | 24540(18.0) | 4.1 | 448 | 57 | (0.14, 0.12) |
| Control 1 | PATSPA: 1% DPAVBi | 6.3 | 7.5 | — | — | — | — | — | (0.14, 0.15) |
| Control 2 | MADN: 5% BD1 | 5.1 | 5.4 | — | — | — | — | — | (0.14, 0.13) |
| Control 3 | PhQ-CVz: 5% BCzVBi | 5.2 | 6.9 | 6.0 | — | — | — | — | (0.16, 0.16) |

According to Table 5, the exemplary deep blue OLED devices using PPP, PTP, TPP and TTP and doped with 5% BCzVBi have achieved better lighting performance (EQE=8.2~6.4%; $\eta_p$=5.3~4.1 lm/W; $\eta_c$=10.2~6.9 cd/A; max brightness=41881 cd/m$^2$; and CIE(x,y)=(0.14, 0.10)) than the control groups 1 to 3.

To sum up, the 9,10-bisphenylphenanthrene derivatives of the present invention may emit blue light and function as a host emitter to be used in an organic light emitting device with advantages such as higher efficiency, lower operating voltage, higher brightness and higher thermal stability.

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. A 9,10-bisphenylphenanthrene derivative, having a structure of formula (1) or (2):

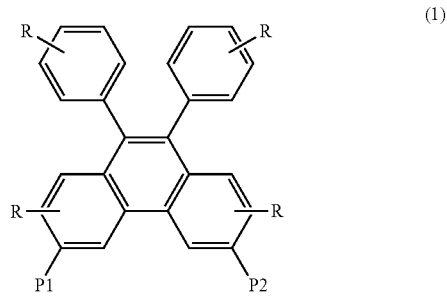
(1)

-continued

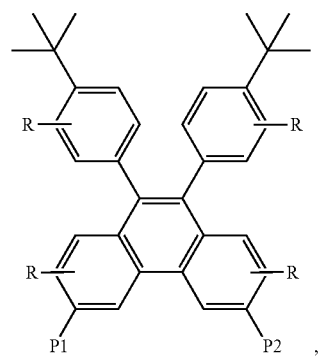
(2)

wherein P1 and P2 are substituted or non-substituted polycyclic aromatic hydrocarbons (PAH) selected from the group consisting of anthracene, benzo[a]pyrane, coronene, corannulene, tetracene, pentacene, phenanthrene, pyrene and ovalene, and R is a member selected from the group consisting of H, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

2. The 9,10-bisphenylphenanthrene derivative of claim 1, wherein each of P1 and P2 is a member selected from the group consisting of anthracene and pyrene.

3. The 9,10-bisphenylphenanthrene derivative of claim 1, wherein P1 and P2 are the same.

4. An organic light emitting diode, comprising:
a cathode;
an anode; and
an emitting layer configured between the cathode and the anode and comprising a 9,10-bisphenylphenanthrene derivative having a structure of formula (1) or (2):

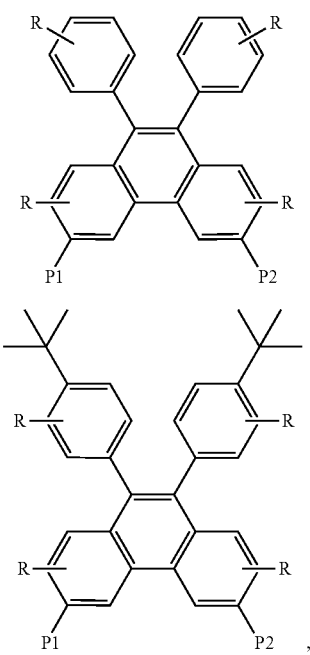

wherein P1 and P2 are substituted or non-substituted polycyclic aromatic hydrocarbons (PAH) selected from the group consisting of anthracene, benzo[a]pyrane, coronene, corannulene, tetracene, pentacene, phenanthrene, pyrene and ovalene, and R is a member selected from the group consisting of H, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

5. The organic light emitting diode of claim 4, wherein each of P1 and P2 is a member selected from the group consisting of anthracene and pyrene.

6. The organic light emitting diode of claim 4, wherein P1 and P2 are the same.

7. The organic light emitting diode of claim 4, wherein the 9,10-bisphenylphenanthrene derivative is a host emitter.

8. The organic light emitting diode of claim 4, wherein the 9,10-bisphenylphenanthrene derivative is a dopant.

9. The organic light emitting diode of claim 4, wherein the organic light emitting diode is a blue organic light emitting diode.

10. The 9,10-bisphenylphenanthrene derivative of claim 1, wherein each of P1 and P2 is a member selected from the group consisting of tetracene, anthracene and pyrene.

11. The organic light emitting diode of claim 4, wherein each of P1 and P2 is a member selected from the group consisting of tetracene, anthracene and pyrene.

* * * * *